United States Patent [19]
Kitamura et al.

[11] Patent Number: 5,081,307
[45] Date of Patent: Jan. 14, 1992

[54] PROCESS FOR PREPARING 2,2-DIMETHOXY-2-PHENYLACETOPHENONE

[75] Inventors: Soichi Kitamura, Tokyo; Masaru Tomioka, Omiya; Hidekuni Gotoh, Ageo, all of Japan

[73] Assignee: Kawaguchi Chemical Co., Ltd., Tokyo, Japan

[21] Appl. No.: 548,133

[22] Filed: Jul. 5, 1990

[30] Foreign Application Priority Data

Jul. 14, 1989 [JP]  Japan ................... 1-180410

[51] Int. Cl.$^5$ ......................... C07C 45/4564
[52] U.S. Cl. ................................ 568/315
[58] Field of Search ........................ 568/315

[56] References Cited

U.S. PATENT DOCUMENTS

| | | | |
|---|---|---|---|
| 4,101,584 | 7/1978 | Ranus et al. | 568/315 |
| 4,190,602 | 2/1980 | Brunisholz et al. | 568/315 |
| 4,287,367 | 9/1981 | Kuesters et al. | 568/315 |
| 4,749,804 | 6/1988 | Schloemer | 568/315 |

FOREIGN PATENT DOCUMENTS

| | | | |
|---|---|---|---|
| 52-125151 | 10/1977 | Japan | 568/315 |
| 56-128729 | 10/1981 | Japan | 568/315 |
| 57-56454 | 11/1982 | Japan | 568/315 |

Primary Examiner—James H. Reamer
Attorney, Agent, or Firm—Frishauf, Holtz, Goodman & Woodward

[57] ABSTRACT 2,2-Dimethoxy-2-phenylacetophenone is prepared by reacting benzil with dimethyl sulfate and alkali metal methylate in a nonpolar organic solvent (e.g. xylene, cyclohexane) in the presence of one or more of catalysts selected from the group consisting of polyethylene glycol, a polyethylene glycol dialkyl ether and a crown ether. The reaction can be carried out more preferably in the presence of diglyme or triglyme or a mixture of diglyme or triglyme and polyethylene glycol.

15 Claims, No Drawings

PROCESS FOR PREPARING 2,2-DIMETHOXY-2-PHENYLACETOPHENONE

BACKGROUND OF THE INVENTION

1. Field of the Invention

This invention relates to a novel process for preparing 2,2-dimethoxy-2-phenylacetophenone.

2,2-Dimethoxy-2-phenylacetophenone is a compound represented by the formula

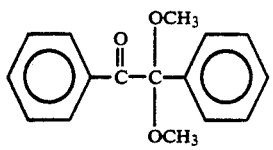

which is widely used as a light sensitizer in polymerization reaction systems in which polymerization is initiated by radical generation with ultraviolet irradiation. Applications of the ultraviolet-cured polymerization-reaction system widely include lithography, flexography, UV-curing ink for silk screens, solder resist, etch resist for materials in electronic industry, finish paints for wood products, metal coating and other various fields.

2. Description of the Prior Art

Heretofore, 2,2-dimethoxy-2 phenylacetophenone has been produced by such processes as a) reaction of benzil with thionyl chloride and methanol (Japanese Patent Publication No. 56456/1982), b) reaction of benzil with methyl orthoformate or methyl orthosilicate (Japanese Patent Application Laid-Open-to-Public No. 128729/1981) and c) reaction of benzil with dimethyl sulfate and sodium methylate (Japanese Patent Application Laid-Open-to-Public No. 125151/1977). The above process a) in which cheap starting materials can be used is associated with operational problems to be solved including the need for complete trapping of sulfurous acid gas formed as a byproduct in addition to the need for distilling off a resulting dimethyl sulfite under reduced pressure. The process b) cannot be considered as economically advantageous because expensive methyl orthoformate or methyl orthosilicate is used. Although the reaction in the process c) proceeds under moderate reaction conditions with materials available at a relatively low cost, i.e. dimethyl sulfate and sodium methylate, the process is disadvantageous in that dehydrative distillation of a dioxane-water azeotrope is required in the dioxane-recovery step due to a large amount of dioxane used as a solvent and a large amount of water added to the reaction mixture.

Moreover, it is common with these prior art techniques that the starting benzil occasionally remains unseparated in the 2,2-dimethoxy-2-phenylacetophenone product, and that use of such impure 2,2-dimethoxy-2-phenylacetophenone occasionally brings yellow staining on the polymer product due to the presence of the benzil.

Therefore, a process for the production of 2,2-dimethoxy-2-phenylacetophenone is needed which eliminates the disadvantages necessarily associated with the conventional process a), b) or c).

The process c) per se may be an acceptable one except for the separation and recovery procedures for the dioxane used because the reaction can proceed under moderate reaction conditions using dimethyl sulfate and sodium methylate both of which are available at a relatively low cost. The reason why dioxane is employed in the process c) as a solvent lies in that benzil is soluble in this solvent and that, therefore, the reaction proceeds in a homogeneous phase. After completion of the reaction dimethyl sulfate and sodium methylate as well as sodium monomethyl sulfate byproduct are to be separated by washing with water, and thus, the dioxane is necessarily diluted with the washings. If water-immiscible solvents such as hydrocarbon solvents could be used, the washing with water and the subsequent solvent-separation step would become much simpler. However, as benzil is hardly soluble in hydrocarbon solvents, a reaction using such solvents will proceed in a heterogeneous phase and the progress of acetalization will be much inhibited. Thus, development of techniques for smoothly progressing the reaction using hydrocarbon solvents is desired.

DETAILED DESCRIPTION OF THE INVENTION

As a result of extensive studies on the reaction of benzil with dimethyl sulfate and an alkali metal methylate using a water-immiscible solvent, we have found that the reaction is much promoted by incorporating in the reaction system an alkylation-promoting agent and/or a polar-increasing agent that is chemically inert to the reactants and the reaction products, which, after completion of the reaction, also much facilitates removal of unreacted alkali metal methylate and sodium monomethyl sulfate of a byproduct from the reaction mixture by washing with water and separation of the solvent, thereby producing 2,2-dimethoxy-2-phenylacetophenone with a high purity and in a high yield by simple procedures. The invention has been completed on the basis of the above finding.

Thus, the invention comprises reacting benzil with dimethyl sulfate and an alkali metal methylate in a nonpolar organic solvent in the presence of one or more of catalysts selected form the group consisting of polyethylene glycol, a polethylene glycol alkyl ether and a crown ether to give 2,2-dimethoxy-2-phenylacetophenone.

As particular examples of the alkali metal methylate are mentioned sodium methylate and potassium methylate. Sodium methylate is preferred because it is available at a lower cost. They may be used either in a solid form or in a form of a concentrated solution, for example, a 28% solution in methanol.

Although, for the reaction in the instant process, ½ mole of dimethyl sulfate and 1 mole of an alkyl metal methylate will be sufficient for 1 mole of benzil, the reaction is usually carried out using somewhat excess amounts of dimethyl sulfate and an alkyl metal sulfate over benzil. Thus, amounts in the range of ½-5 moles, preferably ½-2 moles of dimethyl sulfate and 1-10 moles, preferably 1-4 moles of an alkyl metal methylate are employed per mole of benzil.

The reaction is carried out usually at a temperature of −50° C. to 150° C. and preferably at a temperature of −20° C. to 100° C. Although the reaction time is variable depending upon proportions of the reactants used, reaction temperatures and other conditions such as rate of stirring, the reaction is usually completed within a few hours.

The solvent used in the process must be a nonpolar solvent that is water-immiscible and inert to the reactants and the reaction products. As solvents meeting these conditions can be mentioned aliphatic hydrocarbon solvents such as n-hexane, 2-methylpentane, 2,2-dimethylbutane, heptane, decane, dodecane, petroleum ether and ligroin; alicyclic hydrocarbon solvents such as cyclohexane, cyclopentane, methylcyclopentane, methylcyclohexane, ethylcyclohexane, tetralin and decalin; aromatic hydrocarbon solvents such as benzene, toluene, xylene, ethylbenzene, cumene and mesitylene, and the like. Solvents especially preferably used in the process include heptane, toluene, xylene, cyclohexane and methylcyclohexane.

Polyethylene glycols used as a catalyst in the process are those which have in the polymer ethylene glycol units in the range of 4-210, preferably 4-40 in number, such as those commercially available under the names of polyethylene glycol 400, polyethylene glycol 1000 and polyethylene glycol 1540.

Polyethylene glycol dialkyl ethers as another group of the catalysts used in the process, are polyethylene glycols having in the polymer chain ethylene glycol units in the range of 2-10 in number and with the terminals respectively blocked with an alkyl group of 1-4 carbon atoms such as those which are commercially available under the names of polyethylene glycol dimethyl ether ($n=2-10$), polyethylene glycol diethyl ether ($n=2-8$) and polyethylene glycol di-n-butyl ether ($n=2-8$).

As crown ethers which are a further group of the catalysts used in the process may be mentioned, for example, macrocyclic ether compounds having the recurring unit $+O-CH_2-CH_2+_n$, representative of which are 12-crown 4, 14-crown-5 and 18-crown-6-and benzo-9-crown-3, dibenzo-20-crown- 4 and dibenzo-18-crown-6.

Those catalysts may be used alone or in a combination of two or more of them.

It is especially preferable to use the catalyst in a combination of polyethylene glycol ($n=4-40$) and polyethylene glycol dimethyl ether ($n=2$ or 3, i.e., diglyme or triglyme), wherein diglyme or triglyme is employed in a proportion of 5-20 by volume of the catalyst compound.

These catalysts are used in a proportion of 0.01-0.1 by volume of the nonpolar solvent employed.

The reaction procedures according to the process of the invention will illustratively be described below. To benzil and dimethyl sulfate are added a nonpolar solvent such as xylene and a catalyst such as polyethylene, and, if required, diglyme or triglyme is further added. To the mixture is added with stirring at room temperature powdery sodium methylate in several portions. It is confirmed that vigorous stirring is highly effective on the progress of the reaction. Completion of the reaction is determined by monitoring the amount of unreacted benzil by gas chromatographic analysis after the addition of the sodium methylate, and normally it is when concentration of the benzil becomes in steady state at the lowest level.

After completion of the reaction, water is added to the reaction mixture. Sodium monomethyl sulfate formed and alkaline matters are removed because they are transferred to the aqueous layer. The washing treatment with water is repeated in the same way as above to separate the oil layer. The separated oil layer contains 2,2-dimethoxy-2-phenylacetophenone product and a small amount of unreacted benzil. The unreacted benzil can be removed as an adduct formed by addition of potassium carbonate and trimethyl phosphite to the oil layer as in known processes such as one described in Japanese Patent Publication No. 56456/1982. The oil layer is further repeatedly washed with water and separated. Distillation of the xylene solvent under reduced pressure yields 2,2-dimethoxy-2-phenylacetophenone as a residue which is analytically almost pure. The product thus obtained is a pure product satisfactorily meeting commerical requirements in its crystal form, color, volatiles, etc. If required, conventional recrystallization from a solvent may further be applied.

The process of the invention will be described in more detail in the following examples.

EXAMPLE 1

To 600 ml of xylene were added 105.1 g of benzil and 81.6 g of dimethyl sulfate followed by addition of 5 g of a polyethylene glycol (PEG-400). The mixture was efficiently stirred at room temperature for blending. To the resulting mixture was added 38.4 g of powdery sodium methylate in several portions over 4 hours while maintaining the reaction temperature at 15°-20° C. After the addition, the resulting mixture was aged under the same conditions for 3 hours. To the reaction mixture was then added 200 ml of water for washing. The underlayered aqueous solution was allowed to stand, separated and removed. The oil layer was then washed with two portions of 200 ml of water. The oil layer thus obtained was treated with 11 g of potassium carbonate and 3.5 g of trimethyl phosphite and again washed with 2-3 portions of 200 ml of water. From the resulting oil layer was distilled off xylene under reduced pressure while maintaining the liquid temperature at or below 80° C. There was obtained 113 g of the desired product with a purity of 99.9%, m.p. 65°-66° C. The yield was 88.2% of the theoretical amount based upon benzil.

EXAMPLE 2

To 525 ml of xylene were added 92 g of benzil, 71.5 g of dimethyl sulfate and as a catalyst 0.35 g of a polyethylene glycol (PEG-1000) and 6 g of diglyme. The mixture was thoroughly blended with stirring at room temperature. To the mixture was added 33.6 g of powdery sodium methylate in several portions over 4 hours while maintaining the reaction temperature at 20°-25° C. After the addition, the resulting mixture was aged under the same conditions for 4.5 hours followed by repeated washing with 400 ml of water divided into 2 portions. There was produced approximately 600 ml of an oil layer, to which 10 g of potassium carbonate and 3 g of trimethyl phosphite were added. Then, the mixture was washed twice with 100 ml of water and twice with 200 ml of water. The oil portion was separated and concentrated under reduced pressure while maintaining the liquid temperature at or below 80° C. to remove the xylene. There was obtained as a residue 102 g of the desired product with a purity of 99.9%, m.p. 65°-66° C. The yield was 90.5% of the theoretical amount based upon benzil.

EXAMPLE 3

To 525 ml of xylene were added 92 g of benzil, 71.5 g of dimethyl sulfate and, as a catalyst, 7 g of a polyethylene glycol diethyl ether (PEG-400DE). The mixture was thoroughly blended with stirring at room temperature. To the mixture was added 33.6 g of powdery sodium methylate in several portions over 5 hours while maintaining the reaction temperature at 20°-30° C. After the addition, the resulting mixture was aged under the same conditions for 5 hours followed by repeated washing with 400 ml of water divided into 2 portions. There was produced approximately 600 ml of an oil portion, which was then treated in the same way as in Example 1. There was obtained 98 g (87.3%) of the desired product with a purity of 99.9%, m.p. 65°-66° C.

EXAMPLE 4

To 600 ml of methylcyclohexane were added 92 g of benzil, 71.5 g of dimethyl sulfate and, as a catalyst, 0.35 g of a crown ether (12-crown-4) and 6 g of diglyme. The mixture was thoroughly blended with stirring at room temperature and then treated in the same way as in Example 1. There was obtained 105 g (93.2%) of the desired product with a purity of 99.9%, m.p. 65°-66° C.

EXAMPLE 5

To 600 ml of cyclohexane were added 92 g of benzil and 71.5 g of dimethyl sulfate and, as a catalyst, 0.35 g of polyethylene glycol (PEG-400) and 6 g of triglyme. The mixture was thoroughly blended with stirring at room temperature. To the mixture was added 33.6 g of powdery sodium methylate in several portions over 4 hours while maintaining the reaction temperature at 20°-25° C. The reaction mixture was washed with 400 ml of water divided into 2 portions to give approximately 600 ml of oil. From the resulting oil was distilled off cyclohexane under reduced pressure while maintaining the liquid temperature at or below 80° C. There was obtained 101 g of the desired product with a purity of 99.9%, m.p. 65°-66° C. The yield was 89.5% of the theoretical amount based upon benzil.

What is claimed is:

1. A process for preparing 2,2-dimethoxy-2-phenylacetophenone which comprises reacting benzil with dimethyl sulfate and an alkali metal methylate in a water-immiscible solvent selected from the group consisting of benzene, toluene, xylene, cyclohexane and methylcyclohexane in the presence of one or two catalysts selected from the group consisting of polyethylene glycol, diglyme, triglyme and a crown ether.

2. The process according to claim 1 wherein the catalyst is a mixture of diglyme or triglyme and polyethylene glycol.

3. The process according to claim 1 or 2 wherein the catalyst is polyethylene glycol which has 4–210 of ethylene glycol units in the polymer.

4. The process according to claim 3 wherein the catalyst is polyethylene glycol which is polyethylene glycol 400 or polyethylene glycol 1000.

5. The process according to claim 1 wherein the catalyst is crown ether which is (12-crown-4).

6. The process according to claim 1, wherein the alkali metal methylate is selected from the group consisting of sodium methylate and potassium methylate.

7. The process according to claim 6, wherein ½ to 5 moles of said dimethyl sulfate are utilized per 1 to 10 moles of said alkyl metal methylate.

8. The process according to claim 6, wherein ½ to 2 moles of said dimethyl sulfate are utilized per 1 to 4 moles of said alkyl metal methylate.

9. The process according to claim 7, wherein the process is conducted at a temperature of −50° C. to 150° C.

10. The process according to claim 8, wherein the process is conducted at a temperature of −20° C. to 100° C.

11. The process according to claim 10, wherein the catalyst is polyethylene glycol which has 4 to 40 ethylene glycol units.

12. The process according to claim 10, wherein the catalyst is a crown ether selected from the group consisting of 12-crown-4, 14-crown-5, 18-crown-6, benzo-9-crown-3, dibenzo-20-crown-4 and dibenzo-18-crown-6.

13. The process according to claim 1, wherein the solvent is xylene, the catalyst is a polyethylene glycol which is polyethylene glycol (PEG-400) and the alkali metal methylate is sodium methylate.

14. The process according to claim 2, wherein the solvent is xylene, the catalyst is a mixture of diglyme and polyethylene glycol, the polyethylene glycol is polyethylene glycol (PEG-1000) and the alkali metal methylate is sodium methylate.

15. The process according to claim 10, wherein the catalyst is in a proportion of 0.01 to 0.1 by volume of the solvent.

* * * * *